(12) United States Patent
Hahn et al.

(10) Patent No.: US 12,403,326 B2
(45) Date of Patent: Sep. 2, 2025

(54) SYSTEM FOR CORNEAL CROSS-LINKING AND CORRECTING VISION BY USING LED CONTACT LENS AND EYE DYE

(71) Applicants: PHI BIOMED INC., Seoul (KR); POSTECH ACADEMY-INDUSTRY FOUNDATION, Gyeongsangbuk-do (KR)

(72) Inventors: Sei Kwang Hahn, Seoul (KR); Sang Baie Shin, Gyeongsangbuk-do (KR); Jong Hwan Mun, Seoul (KR)

(73) Assignees: PHI BIOMED INC., Seoul (KR); POSTECH ACADEMY-INDUSTRY FOUNDATION, Gyeongsangbuk-do (KR)

( * ) Notice: Subject to any disclaimer, the term of this patent is extended or adjusted under 35 U.S.C. 154(b) by 846 days.

(21) Appl. No.: 17/642,565

(22) PCT Filed: Sep. 11, 2020

(86) PCT No.: PCT/KR2020/012280
§ 371 (c)(1),
(2) Date: Mar. 11, 2022

(87) PCT Pub. No.: WO2021/049898
PCT Pub. Date: Mar. 18, 2021

(65) Prior Publication Data
US 2022/0323780 A1    Oct. 13, 2022

(30) Foreign Application Priority Data

Sep. 11, 2019 (KR) .................. 10-2019-0112695
Apr. 13, 2020 (KR) .................. 10-2020-0044528

(51) Int. Cl.
*A61N 5/06* (2006.01)
*A61K 51/04* (2006.01)
*G02C 7/04* (2006.01)

(52) U.S. Cl.
CPC .......... *A61N 5/062* (2013.01); *A61K 51/0497* (2013.01); *G02C 7/049* (2013.01); *A61N 2005/0645* (2013.01); *A61N 2005/0651* (2013.01); *A61N 2005/0663* (2013.01)

(58) Field of Classification Search
CPC ........... A61K 8/73; A61Q 19/00; A61B 18/20
USPC ....................................................... 424/427
See application file for complete search history.

(56) References Cited

U.S. PATENT DOCUMENTS

2013/0211389 A1 *  8/2013  Chuck .................. A61P 27/02
                                                               606/5

FOREIGN PATENT DOCUMENTS

WO    WO-2012087040 A2 *  6/2012  ........... A61K 31/555

* cited by examiner

*Primary Examiner* — Walter E Webb
(74) *Attorney, Agent, or Firm* — Myers Bigel, P.A.

(57) ABSTRACT

The present invention relates to a system for corneal cross-linking of injured corneas, treating keratoconus, or correcting vision, the system comprising: a hyaluronic acid-dye conjugate; and a contact lens including an LED light source. In the present invention, a dye is activated by receiving light irradiated from the LED light source of the contact lens so as to generate radicals, thereby generating a covalent bond between amino acid radicals of corneal collagen, and strengthening a collagen layer. In the present invention, the hyaluronic acid-dye conjugate, in which hyaluronic acid is bound to the dye, is used to improve penetration of the dye in the cornea, and the contact lens is used together with the hyaluronic acid-dye conjugate to further improve the penetration of the dye. In addition, the structure of the lens which presses the center of the cornea deforms the shape of the cornea, thereby having a vision correction effect.

10 Claims, 9 Drawing Sheets

Fabricated Smart LED Lens

LED Smart contact lens

Photonic Lens

SYSTEM FOR CORNEAL CROSS-LINKING AND CORRECTING VISION BY USING LED CONTACT LENS AND EYE DYE

TECHNICAL FIELD

The present invention relates to a system for corneal crosslinking and vision correction by using an LED contact lens and an ocular dye.

BACKGROUND

Keratoconus is an eye disease that occurs by thinning and protrusion of the cornea, greatly affecting vision. This may be caused by genetic factors, excessively rubbing the eyes and UV exposure, and result in, for example, reduced contrast sensitivity, decreased vision, irregular astigmatism, glare, and distortion. Methods of treating this include the use of tools such as corrective glasses or corrective contact lenses, and surgical methods such as corneal transplantation and intracorneal ring insertion.

In particularly, while, in the beginning, correction is possible to some extent by wearing corrective glasses, after a certain period of time, it is impossible to correct vision with glasses, and hard lenses for keratoconus treatment must be worn (Patent Document 1). Hard lenses have a flat central portion, and when the lenses are worn, the wearer's corona is temporarily deformed to correct vision. Particularly, vision correction is possible for myopia and irregular astigmatism. However, there is a disadvantage that the correction effect is temporarily maintained during detachment, so it is not permanent. As a surgical method, there is a method of reducing irregular astigmatism by inserting a semicircular ring into the corneal stroma, or a method of exposing the corneal surface. However, the surgical method may cause a patient to feel a foreign body or to be reluctant to have an operation that exposes the cornea.

Therefore, there is a need for a novel treatment or procedure, which can effectively and safely treat keratoconus and not burden a patient with regular wearing or surgery.

RELATED ART DOCUMENT

Patent Document

1. Korean Patent Publication No. 10-1199425

DISCLOSURE

Technical Problem

The present invention relates to a system for corneal crosslinking and vision correction by using an LED contact lens and an ocular dye.

Technical Solution

The present invention provides a system for injured cornea crosslinking, keratoconus treatment or vision correction, which includes:
a hyaluronic acid-dye conjugate; and
a contact lens including an LED light source.

The present invention also provides a method for injured cornea crosslinking, keratoconus treatment or vision correction by using the above-described system for injured cornea crosslinking, keratoconus treatment or vision correction, which includes: applying a hyaluronic acid-dye conjugate to a subject's cornea;
wearing a contact lens including an LED light source; and
irradiating the subject's cornea with light emitted from the LED light source in the contact lens.

Advantageous Effects

The present invention provides a system for injured cornea crosslinking, keratoconus treatment or vision correction, which includes a hyaluronic acid-dye conjugate; and a contact lens including an LED light source.

In the present invention, the dye can be activated by receiving light applied from an LED light source of a contact lens, thereby generating radicals, and therefore, a covalent bond between amino acid radicals can be made between corneal collagen, which strengthens a collagen layer. In the present invention, the hyaluronic acid-dye conjugate in which hyaluronic acid is bonded to the dye can be used to enhance the permeability of a dye into the cornea, and also used with a contact lens to further enhance dye permeability. Moreover, since the contact lens has a structure that presses the center of the cornea, it can deform the shape of the cornea, thereby having a vision correction effect.

The system according to the present invention can be used in crosslinking of injured corneas and treatment of keratoconus or an injured cornea, and also be used for a wide range of vision correction.

MODES OF THE INVENTION

The present invention relates to a system for injured cornea crosslinking, keratoconus treatment or vision correction, which includes a hyaluronic acid-dye conjugate; and a contact lens including an LED light source.

Hereinafter, the system for crosslinking of injured corneas, keratoconus treatment or vision correction will be described in further detail.

In the present invention, a collagen crosslinking procedure (also referred to as corneal collagen crosslinking) is a therapeutic method designed to strengthen a weakened cornea so that the eye no longer moves forward. The cornea consists of collagen. Collagen structures are not separated but are interlocked with each other, and when the binding strength of the structures is not strong, the cornea cannot maintain its original shape and is deformed. In the case of keratoconus, such a binding strength is lower than normal. Therefore, keratoconus may be treated by increasing the binding strength of collagen.

In addition, the collagen crosslinking procedure is performed by allowing a dye to permeate into the cornea in order to increase the binding strength of collagen, and then irradiating the cornea into which the dye permeated with UV rays. That is, in the case of the collagen crosslinking procedure, corneal bonding may be made by crosslinking between corneal collagen. Here, the "crosslinking" refers to making chemical linkages between molecular chains in collagen fibers. In addition, the "corneal bonding" means forming crosslinks in corneal collagens. The corneal collagen crosslinking may enhance mechanical properties of the weakened cornea, and may treat keratoconus resulting in a thin cornea. In addition, a vision correction effect may be achieved through the collagen crosslinking procedure.

The system for injured cornea crosslinking, keratoconus treatment or vision correction according to the present invention includes a hyaluronic acid-dye conjugate; and a contact lens including a LED light source.

In the present invention, the hyaluronic acid-dye conjugate is a compound in which hyaluronic acid and a dye are chemically bonded.

In the present invention, since hyaluronic acid has not only biocompatibility and biodegradability but also a transdermal delivery property, there are advantages in that it can be safely applied to the human body and can be applicable to transdermal drug delivery systems for various protein drugs including antigenic proteins and chemical drugs.

Unless clearly stated otherwise, "hyaluronic acid (HA)" refers to a polymer having a repeating unit represented by Formula 1 below and encompasses all hyaluronic acid salts and derivatives thereof.

[Formula 1]

In Formula 1, n may be an integer of 25 to 10,000.

The "hyaluronic acid derivative" used herein encompasses all hyaluronic acid variants in which a functional group such as an amine group, an aldehyde group, a vinyl group, a thiol group, an aryloxy group, N-succinimidyl-3-(2-pyridyldithio)propionate (SPDP) or N-hydroxysuccinimide (NHS) is introduced to the basic structure of the hyaluronic acid of Formula 1. For example, as the hyaluronic acid derivative, HA-diaminobutane, HA-hexamethylenediamine, HA-aldehyde, HA-adipic acid dihydrazide (HA-ADH), HA-2-aminoethyl methacrylate hydrochloride, HA-spermine HA-spermidine, HA-SPDF or HA-NHS may be used.

The hyaluronic add is a linear polysaccharide polymer, which is present in most animals and has biodegradability, biocompatibility and no immune response, and may be safely applied to the human body. The hyaluronic add may be used for various purposes since it plays several different roles in the body according to its molecular weight.

The hyaluronic acid, a hyaluronic acid salt or a hyaluronic acid derivative used in the present invention has no limitation to its composition, but preferably has a molecular weight of 10,000 to 3,000,000 daltons (Da). The hyaluronic acid, a hyaluronic acid salt or a hyaluronic acid derivative, which has a molecular weight in the above-described range, is suitable for use in a conjugate for drug delivery.

The dye in the present invention may generate radicals through irradiation with light emitted from an LED light source of a contact lens to be described below, and therefore, corneal bonding may be made.

The type of dye is not particularly limited, and may be an ocular dye. As the ocular dye, one or more selected from the group consisting of Rose Bengal, riboflavin, ethyl eosin, eosin Y, fluorescein, 2,2-dimethoxy, 2-phenylacetophenone, 2-methoxy, 2-phenylacetophenono, camphorquinone, methylene blue, erythrosine, Floxime, thionine and methylene green may be used.

In the present invention, as the dye, Rose Bengal or riboflavin may be used. When riboflavin is activated by irradiation with light having a wavelength of 354 nm, or Rose Bengal is activated by irradiation with light having a wavelength of 532 nm, radicals may be generated, and due to this, a covalent bond between amino acid radicals may be formed between corneal collagens, strengthening the collagen layer.

In one embodiment, the hyaluronic acid-dye conjugate is a conjugate in which a carboxyl group of hyaluronic acid and a carboxyl group of a dye are bonded through a linker.

As the linker, a diamine compound may be used, and the diamine compound may be one or more selected from the group consisting of diaminohexane (hexamethylenediamine), ethylenediamine, butylenediamine, pentaethylenehexaamine, and 1,5-diamino-2-methylpentane.

In the present invention, the permeability of a dye into the cornea may be enhanced by using the hyaluronic acid-dye conjugate in which a dye and hyaluronic acid are bonded.

In the present invention, the contact lens may be based on one or more polymers selected from the group consisting of an elastomer such as a silicone elastomer, silicone hydrogel; polydiemthyloxane (PDMS); poly(2-hydroxyethylmethacrylate (PHEMA); and polyethylene glycol) methacrylate (PELMA).

In one embodiment, the contact lens may be one in which an LED light source is introduced to a conventional contact lens used for vision correction, or may be fabricated in a laboratory.

In one embodiment, the contact lens may have a structure in which its surface, specifically, the center, is flat so that, when worn, the wearer (target)'s cornea may be temporarily deformed to correct vision.

In the present invention, the contact lens includes an LED light source. In the present invention, the subject's cornea may be stably irradiated with light by applying such a light source to the contact lens.

In one embodiment, the LED light source may be a microLED (mLED or μLED).

The LED light source, that is, the microLED, may be a product generally used in the art, or may be directly manufactured and used.

In one embodiment, the LED light source may emit light onto the cornea. In the hyaluronic acid-dye conjugate applied to a subject before wearing the contact lens, the dye may generate radicals by receiving the light, thereby performing corneal collagen bonding.

In one embodiment, the LED light source may be configured by selecting LEDs emitting light with a specific wavelength according to the purpose of use. For example, the LED light source may emit light with a wavelength of 350 to 550 nm, 350 to 380 nm or 520 to 550 nm.

In addition, in one embodiment, the position of the LED light source in the contact lens is not particularly limited, and its position may be suitably adjusted.

In one embodiment, a transparent substrate may be formed in the contact lens, and the LED light source may be formed on the transparent substrate.

The transparent substrate may have excellent light transmittance, flexibility and elasticity. In addition, the transparent substrate has excellent biocompatibility. Such a transparent substrate may include one or more selected from the group consisting of parylene C, PDMS, a silicone elastomer, polyethylene terephthalate (PET) and polyimide (PI).

In one embodiment, the LED light source may be formed on the ocular side of the transparent substrate.

The contact lens of the present invention may further include one or more selected from the group consisting of an application-specific integrated circuit (ASIC), a battery and an antenna in addition to the above-described LED light source.

In one embodiment, the ASIC may be used for wireless control of the LED light source and power transmission. Such ASIC may be composed of a digital control, a relaxation oscillator, a carrier frequency generator, a bandgap reference generator and a Vdd generator. The ASIC may be fabricated and used depending on a desired use.

In one embodiment, the battery may be a thin film-type battery which is rechargeable and flexible. The wireless driving of the contact lens is possible using the thin film-type battery, and it is also possible to implement a system that can be operated without external power supply.

The battery may supply power to elements that constitute the contact lens. In addition, there is no damage to the battery even with repeated bending or deformation, and when applied to the lens, the battery is sealed, and intraocular stability may be secured. The thin film-type battery may be a product that can be used in the art, or may be directly manufactured and used.

In one embodiment, the antenna may transmit and receive power and a signal to and from the outside through an induced current and electromagnetic resonance. The antenna may be a circular antenna having a circular structure.

The antenna may consist of a nanomaterial, which may be one or more selected from the group consisting of a metal thin film material; a zero-dimensional material such as nanoparticles; a one-dimensional nanomaterial such as a nanowire, a nanofiber or a nanotube; and a two-dimensional nanomaterial such as graphene, $MoS_2$ or a nanoflake. Specifically, the antenna may include a silver nanowire or a silver-gold core-shell nanowire (Ag—Au core-shell NW).

In one embodiment, the antenna may include a wireless antenna for receiving power generated from the outside, that is, wireless power, and a radio frequency antenna for data communication.

Particularly, in the present invention, the wireless antenna may supplement the role of the battery. The wireless electric antenna may receive power generated from a wireless electric coil of smart glasses to be described below. The received power may be used for driving of the LED light source through ASIC control.

In one embodiment, the above-described ASIC, battery and antenna may be formed on a transparent substrate to facilitate fabrication and driving. The ASIC, battery and antenna may be formed on the ocular side of the transparent substrate, that is, the same side as the LED light source.

In the present invention, the contact lens including an LED light source may be fabricated by (S1) forming a sacrificial layer soluble in water on a handling substrate;
 (S2) forming a transparent substrate on the sacrificial layer;
 (S3) forming an LED light source on the transparent substrate; and
 (S4) transferring the transparent substrate on which the LED light source is formed into the contact lens.

Step (S1) is to form a sacrificial layer on a handling substrate.

The sacrificial layer may play the role of an adhesive between the handling substrate and the transparent substrate, and may help the transfer of the transparent substrate on which the LED light source is formed. Such a sacrificial layer is not particularly limited as long as it is capable of being dissolved in water, and may include one or more selected from the group consisting of PVA and dextran.

Step (S2) is to form a transparent substrate on the sacrificial layer, and the sacrificial layer serves as an adhesive. Accordingly, the transparent substrate may be easily adhered to a handling substrate and may be easily detached from the handling substrate through the dissolution of the sacrificial layer in a subsequent process.

In one embodiment, the transparent substrate may employ a material having excellent light transmittance, and the above-described type may be used.

Step (S3) is to form an LED light source on the transparent substrate.

In one embodiment, the LED light source may be bonded to the transparent substrate using human-compatible epoxy, for example, Ag epoxy.

In addition, Step (S4) is to transfer the transparent substrate on which the LED light source is formed into the contact lens.

The LED light source formed on the sacrificial layer may be transferred while the sacrificial layer is dissolved in water, which is biocompatible.

In addition, the present invention may further include forming ASIC, a battery and an antenna on the transparent substrate. This step may be performed during Step (S3).

In one embodiment, the ASIC may be fabricated by depositing a metal such as gold or aluminum on a transparent substrate, and then forming a metal pad by an etching method using photolithography; and
 bonding the element to the metal pad through a flip-chip bonding process.

In the flip-chip bonding process, the element may be bonded through an ultrasonic and heat compression process using a non-conductive adhesive.

In one embodiment, the battery may be formed on the transparent substrate by the same method as used for the LED light source.

In addition, in one embodiment, the antenna may be fabricated by:
 (a1) forming a mask material for patterning on a transparent substrate;

(a2) patterning a sensor and a circuit by coating the transparent substrate on which the mask material is formed with a nanomaterial through a lift-off process; and (a3) forming a passivation layer on the patterned sensor and circuit.

Step (a1) is to form a mask material for patterning on a transparent substrate.

The mask material may serve as a shadow mask to pattern the nanomaterial. As such a mask material, a material that can be used as a photoresist may be used, and specifically, LOF and the AZ series may be used.

Step (a2) is to pattern a sensor and a circuit by coating the transparent substrate on which the mask material is formed with a nanomaterial through a lift-off process.

A pattern of the nanomaterial may be formed according to the above-described step. The nanomaterial may employ the above-described type, and specifically, a silver nanowire or a silver-gold core-shell nanowire (Ag—Au core-shell NW) may be used.

The nanomaterial prepared in the above-described step may serve as an antenna.

In addition, the circuit fabricated in the above-described step may serve to connect an LED light source, a semiconductor element, an antenna and a battery.

Step (a3) is to form a passivation layer on the patterned antenna and circuit.

The passivation layer may be formed to prevent the loss of the nanomaterial and improve electrical stability.

In addition, the system of the present invention may further include smart glasses.

In the present invention, the smart glasses may control the driving of the LED light source of the contact lens by wirelessly transmitting or receiving an electrical signal. The smart glasses may employ a rechargeable lithium-ion battery as driving power, and perform wireless communication with a smart device using a Bluetooth module in the smart glasses.

The smart glasses may be paired with a smartphone, a smart watch or a PC. For power, a built-in lithium-ion battery may be used, and a photocell may be inserted for self-powering. The total weight of the smart glasses may be less than 20 g, and Wi-Fi 802.11b/g, Bluetooth and microUSB may be available.

The system according to the present invention may be used in injured cornea crosslinking, and keratoconus treatment. In addition, the system according to the present invention may be used in vision correction.

In addition, the present invention relates to a method for injured cornea crosslinking, keratoconus treatment or vision correction by using the above-described system for injured cornea crosslinking, keratoconus treatment or vision correction.

The method according to the present invention includes:
(A) applying a hyaluronic acid-dye conjugate to a subjects cornea;
(B) wearing a contact lens including an LED light source; and
(C) irradiating the subject's cornea with light emitted from the LED light source in the contact lens.

Step (A) is to apply a hyaluronic acid-dye conjugate to a subject's cornea. The hyaluronic acid-dye conjugate may be prepared in the form of a liquid composition for an eye drop medication, and may be applied to the cornea by a method of dropping (loading) on the cornea.

A conventional ocular dye is directly administered to the corneal stroma after surgical removal of the corneal epithelial layer. In the present invention, the dye may be applied to the cornea without surgery for removing the corneal epithelial layer by bonding hyaluronic acid to the ocular dye. The conjugate may be successfully delivered to the corneal stroma in which collagen is abundantly distributed through the corneal epithelial layer, and therefore may have high permeability into the cornea.

Step (B) is to wear a contact lens including an LED light source. The contact lens including the LED light source according to the present invention may have the same structure as a conventional lens for vision correction, and specifically, have a flat center. Due to this structure, when the lens is worn, it is configured to press the center of the cornea to deform the shape of the cornea, which is effective in vision correction. In addition, when the hyaluronic acid-dye conjugate was loaded on the corneal surface, and the contact lens was worn, the hyaluronic acid-dye conjugate may be more easily permeated into the corneal stroma due to a wearing pressure.

Step (C) is to irradiate the subject's cornea with light emitted from the LED light source in the contact lens.

Through this step, the dye may be activated by receiving light emitted from the LED light source of the contact lens to generate radicals, and therefore, a covalent bond between amino acid radicals may be formed between corneal collagen, and a collagen layer may become stronger.

Particularly, in the present invention, as the hyaluronic acid-dye conjugate and the contact lens with a flat surface are used, more effective crosslinking of the corneal collagen layer may be induced by emitting light with a specific wavelength toward the cornea from the LED light source, thereby extending the effect of vision correction compared to the conventional lens.

In one embodiment, the wavelength of light emitted from the LED light source may be 350 to 550 nm, 350 to 380 nm, or 520 to 550 nm. The irradiation time may vary according to the amount of light, and may be, for example, 200 to 800 seconds.

In one embodiment, the method of the present invention may additionally employ smart glasses. The wireless power, which is generated from the wireless electrical coil of the smart glasses may be received by a wireless electrical antenna of the contact lens, and the power received through ASIC control may be used in driving of the LED light source.

Hereinafter, the present invention will be described in detail with reference to the following examples. The following examples are merely provided to exemplify the present invention, and the contents of the present invention are not limited to the following examples.

EXAMPLES

Example 1. Preparation of Hyaluronic Acid-Ocular Dye Conjugate 500 mg of hyaluronic acid (100 kDa) and 2.89 g of diaminohexane were added to a sodium acetate buffer with a pH of 4.8, and 1-ethyl-3-(3-dimethylaminopropyl)carbodiimide (EDC) was added, followed by a reaction for 5 minutes.

Subsequently, Rose Bengal was added at a concentration two times the molar concentration of diaminohexane, and EDC and N-hydroxysuccinimide were added in excess. The reaction was carried out for 12 hours at room temperature while the pH of the solution was maintained at 4.8 with hydrochloric acid and sodium hydroxide. After purification in distilled water for one week, the final solution was freeze-dried for three days, thereby preparing a hyaluronic acid-Rose Bengal conjugate.

Experimental Example 1. Confirmation of Preparation of Hyaluronic Acid-Rose Bengal Conjugate 1) Method In order to confirm the hyaluronic acid-Rose Bengal conjugate synthesized in Example 1, absorbance measurement and FT-IR analysis of the prepared conjugate were performed.

2) Results

Figure 1:
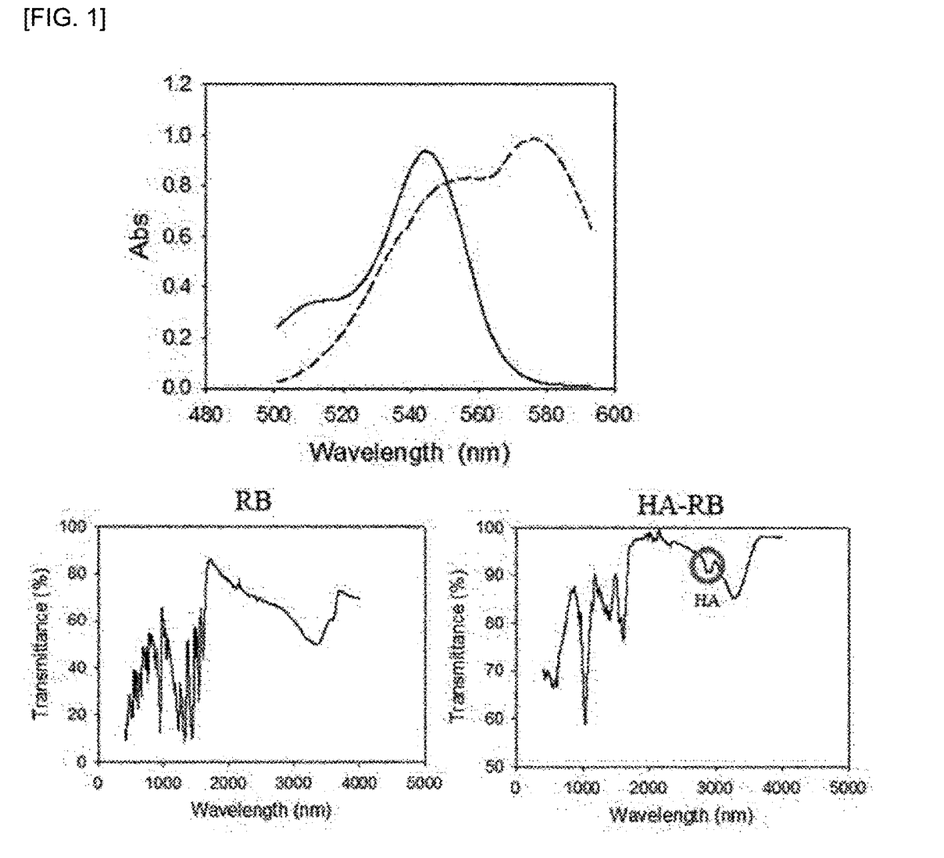
FIG. 1 shows absorbance and FT-IR analysis results for a hyaluronic acid-Rose Bengal conjugate synthesized in an example.

FIG. 1 shows absorbance and FT-IR analysis results for the hyaluronic acid-Rose Bengal conjugate.

First, the upper graph of FIG. 1 shows the absorbance of the hyaluronic acid-Rose Bengal conjugate, showing that the peak of Rose Bengal can shift from 540 nm to 580 nm. In addition, the lower graphs of FIG. 1 show the FT-IR analysis results for pure Rose Bengal (left) and the hyaluronic acid-Rose Bengal conjugate (right), confirming that a peak that is not observed in the pure Rose Bengal is observed near 3000 nm. Accordingly, it can be confirmed that the hyaluronic acid-Rose Bengal conjugate was successfully synthesized.

Experimental Example 2. Analysis of Corneal Permeability of Hyaluronic Acid-Rose Bengal Conjugate 1) Method The hyaluronic acid-Rose Bengal conjugate synthesized in Example 1 was dropped on the bovine cornea at 5-minute intervals for 30 minutes. As a comparative group, a pure Rose Bengal solution was dropped in the same manner as described above.

Afterward, two-photon image analysis was performed by extracting the cornea from the bovine cornea.

2) Results

Figure 2:
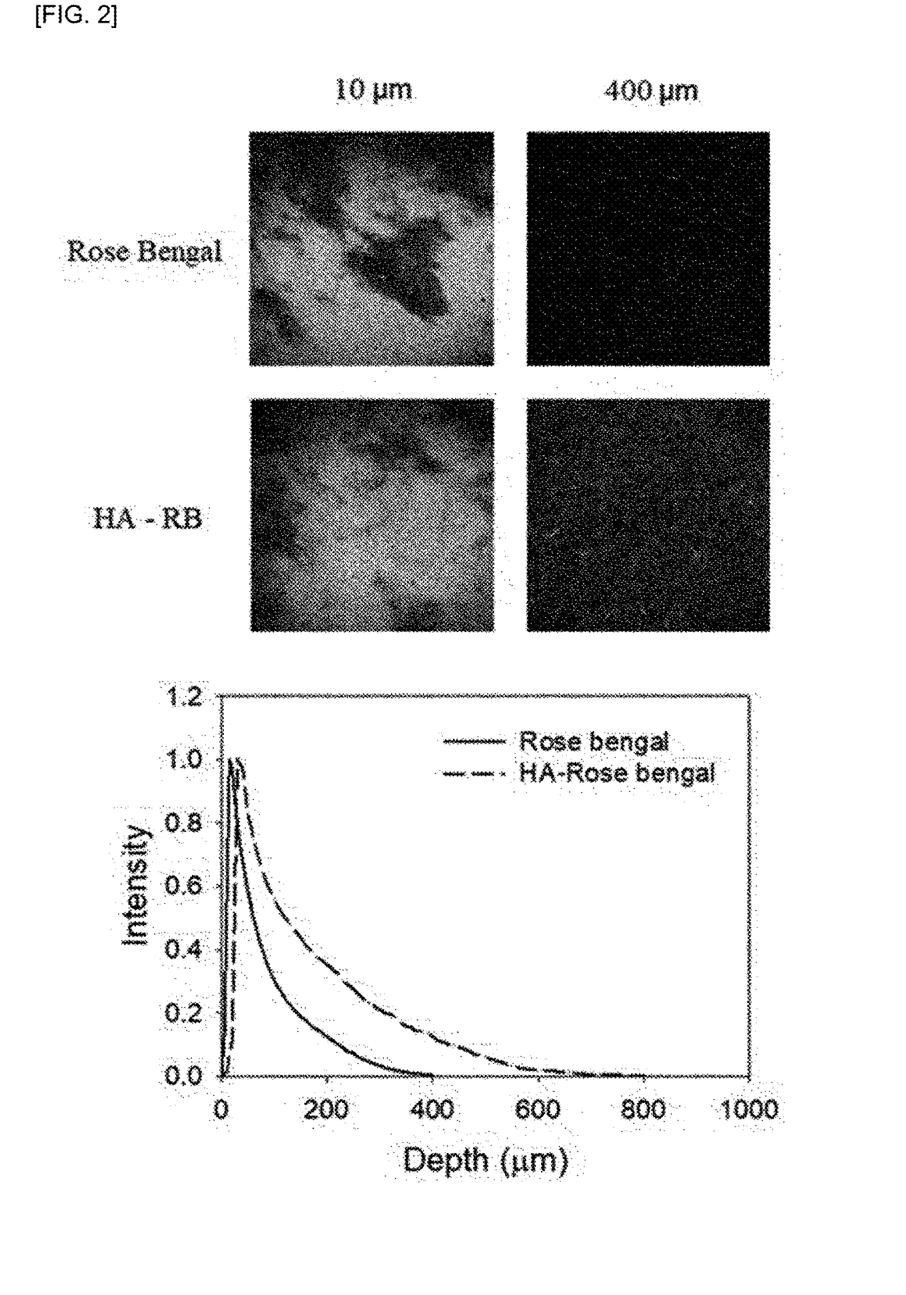
FIG. 2 shows two-photon images and a graph, which analyze the degree of corneal permeability of a hyaluronic acid-Rose Bengal conjugate and Rose Bengal.

FIG. 2 shows images and a graph, which analyze the degree of corneal permeability of a hyaluronic acid-Rose Bengal conjugate and Rose Bengal.

As shown in FIG. 2, when the hyaluronic acid-Rose Bengal conjugate was used, it was confirmed that fluorescence was shown up to 620 μm, and when Rose Bengal was used, fluorescence was shown up to 400 μm. Accordingly, it can be confirmed that when hyaluronic acid is conjugated to Rose Bengal, the permeability to the cornea is further increased.

Experimental Example 3. Analysis of Corneal Bonding by Hyaluronic Acid-Rose Bengal Conjugate 1) Method After approximately 6.4-cm wound was made in the bovine cornea, the pressure in the bovine eye was measured using a tonometer. Afterward, each of a hyaluronic acid-Rose Bengal conjugate solution and a Rose Bengal solution was dropped on the wound-induced region at 5-minute intervals for 30 minutes, and a 532-nm laser was irradiated for 30 minutes to induce crosslinking between corneal collagen to bond. Likewise, an intraocular pressure was measured after bonding by a laser using a tonometer.

By comparing the intraocular pressure before and after bonding, it was confirmed whether bonding was formed.

2) Results

Figure 3:
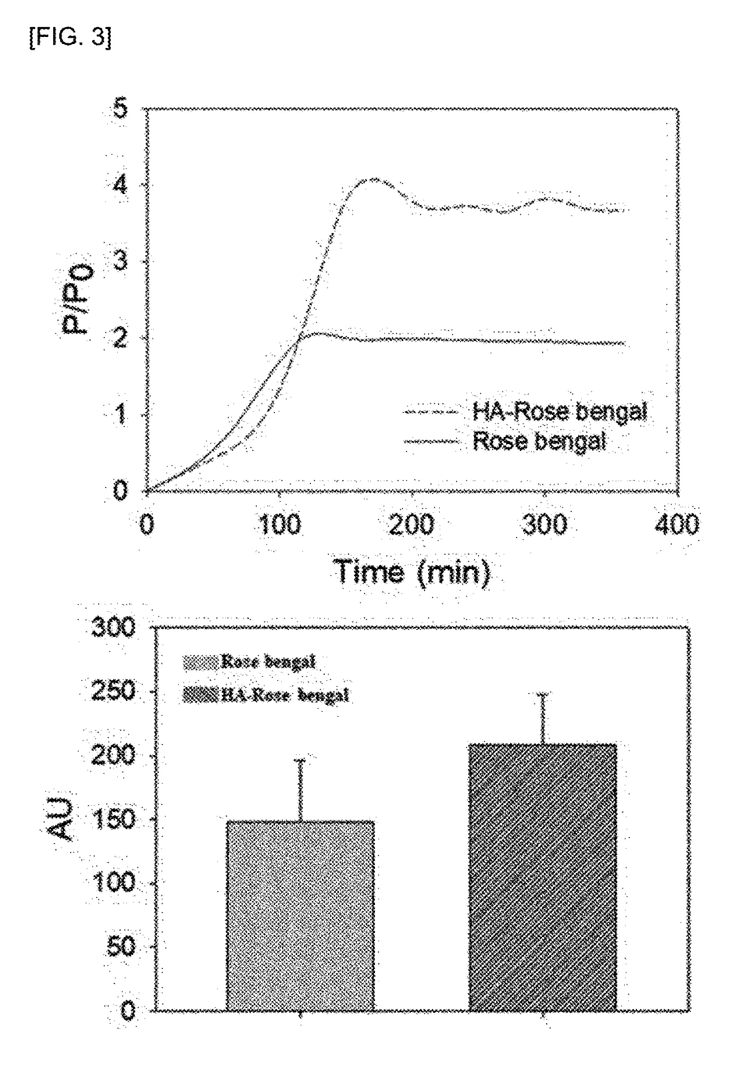
FIG. 3 shows a rate of change in intraocular pressure in a bovine eye, which is treated using Rose Bengal and a hyaluronic acid-Rose Bengal conjugate, and a rate of increase in maximum intraocular pressure compared to a control.

FIG. 3 shows a rate of change in the intraocular pressure in a bovine eye treated with a hyaluronic acid-Rose Bengal conjugate solution and a Rose Bengal solution.

As shown in FIG. 3, it can be confirmed that, when Rose Bengal was treated, the maximum intraocular pressure increased approximately two-fold compared to when Rose Bengal was not treated, and when the hyaluronic acid-Rose Bengal conjugate was treated, the maximum intraocular pressure increased approximately 3.5-fold. Accordingly, it can be confirmed that when the hyaluronic acid-Rose Bengal conjugate was treated, more effective corneal crosslinking is possible.

Experimental Example 4. Analysis of Corneal Shaping and Strength Change Using Hyaluronic Acid-Rose Bengal Conjugate 1) Method Hyaluronic acid or a hyaluronic acid-Rose Bengal conjugate were dropped on the bovine cornea at 5-minute intervals for 30 minutes, and a 532-nm laser was irradiated for 30 minutes to induce crosslinking between corneal collagen. Afterward, corneal tissue was fixed with formalin, and stained with H&E, followed by observation under a microscope.

In addition, the bovine cornea in which collagen crosslinking was induced was extracted, and then the Young's modulus of the cornea was measured using Instron equipment to analyze the strength of the cornea.

2) Results

Figure 4:
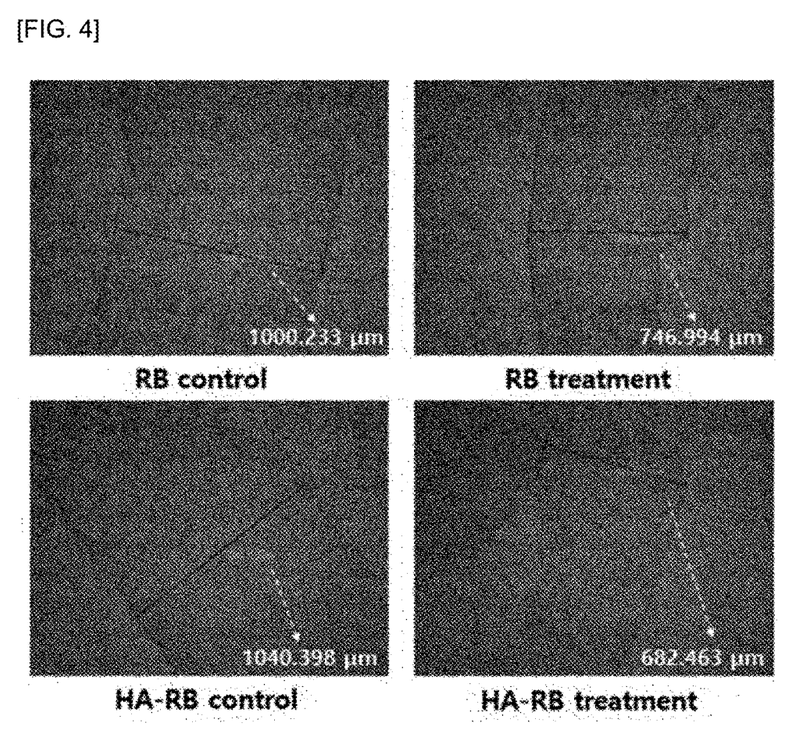
FIG. 4 shows results of analyzing the thicknesses of corneas from images of corneas stained with H&E.

FIG. 4 shows images of corneal tissue stained with H&E. In addition, the corneal thickness was analyzed using the images of FIG. 4.

As shown in FIG. 4, it can be confirmed that when Rose Bengal was treated, the corneal thickness decreased from 1000 μm to 750 μm, and when the hyaluronic acid-Rose Bengal conjugate was treated, the corneal thickness decreased from 1000 μm to 680 μm. Accordingly, it can be confirmed that, when the hyaluronic acid-Rose Bengal conjugate was used, the collagen layers in the cornea are well crosslinked to be firmly crosslinked.

Figure 5:
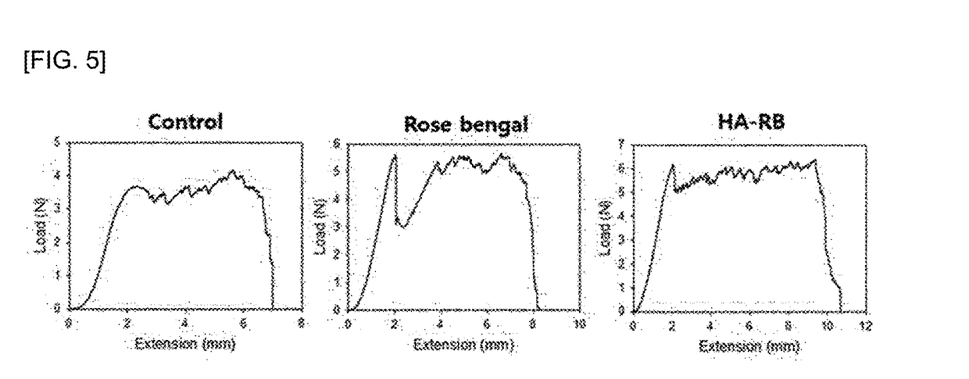
FIG. 5 shows the tensile strength of a cornea that is measured using Instron equipment and an applied load.

Meanwhile, FIG. 5 is a set of graphs showing a length that extends when the cornea is pulled with a constant strength using Instron equipment.

As shown in FIG. 5, as a result of analyzing the Young's modulus, it can be confirmed that, in the case of a comparative group (Control) not treated with the conjugate, the Young's modulus is 1.76, in the case treated with Rose Bengal, the Young's modulus is 2.75, and in the case treated with the hyaluronic acid-Rose Bengal conjugate, the Young's modulus is 3.1. Accordingly, when the hyaluronic acid-Rose Bengal conjugate was treated, it can be confirmed that, in fact, bonds between the corneal collagen layers are made, making the layers stronger.

Example 2. Fabrication of Contact Lens

As a light source for injured cornea crosslinking, keratoconus treatment or vision correction by using the hyaluronic acid-dye conjugate of Example 1, an LED-equipped smart contact lens was fabricated as follows.

(1) Design and Fabrication of ASIC

For wireless control and power transmission of an LED light source, an ASIC including a circuit composed of a digital control, a relaxation oscillator, a carrier frequency generator, a bandgap reference generator, and a Vdd generator is needed. By using the ASIC, it is possible to wirelessly transmit power and drive a contact lens, and control current and light irradiation timing. As the light source, UV-, blue-, green-, red- and IR-emitting LEDs may be applied.

Figure 6A:
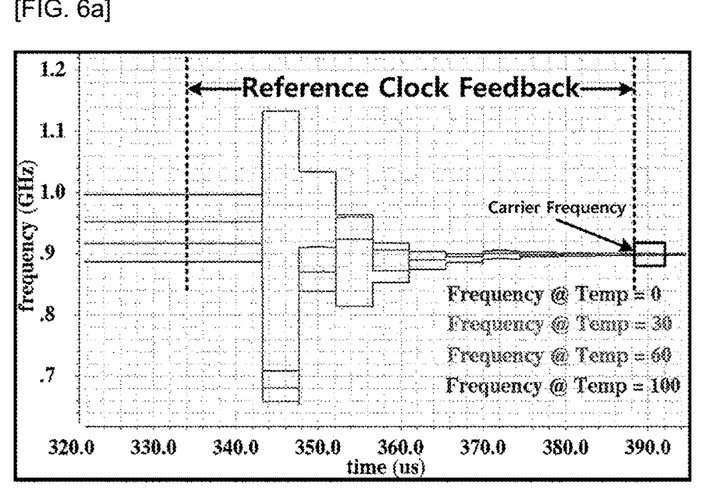
FIGS. 6A and 6B illustrate the fabrication of an application-specific integrated circuit (ASIC), and show the computer simulation, layout and final test results for the chip.
Figure 6B:
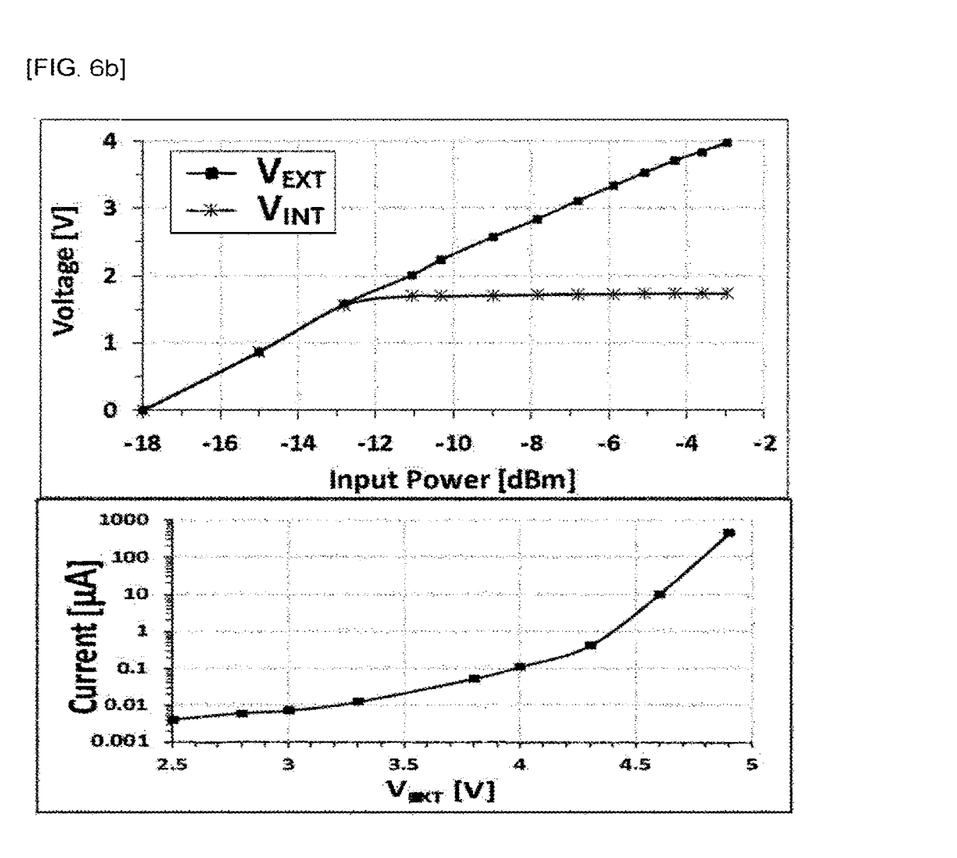

As shown in FIG. 6, the ASIC can be fabricated through computer simulation (the upper graph of FIG. 6A), layout generation (the lower diagram of FIG. 6A) and TOAD simulation (final test; FIG. 6B), and considering self-power consumption; it was fabricated by a CMOS process of 0.18 μm or less. In addition, the fabricated ASIC chip was mounted on a printed circuit board (PCB) to perform the final test.

(2) Fabrication of Contact Lens

A contact lens was fabricated using the ASIC fabricated in (1) and the LED light source.

The contact lens of the present invention was fabricated through metal deposition, photolithography, flip chip bonding, LED bonding and contact lens fabrication.

Specifically, a metal such as gold or aluminum was deposited on a flexible transparent substrate having a thickness of 30 μm or less to a thickness of 200 to 500 nm, and a pad was formed by a wet/dry etching method using photolithography. Afterward, by using a flip-chip bonding process, the ASIC was bonded to the flexible transparent substrate using a non-conductive adhesive through an ultrasonic and heat compression process. A LED light source, a battery, a capacitor and resistor for voltage and current control were bonded using human-compatible epoxy (Ag epoxy) in consideration of thermal resistance of the flexible plastic substrate.

Only an element part was cut from the transparent substrate to which each element was bonded using a laser cutter, and a lens was fabricated with a human-compatible Si elastomer.

Subsequently, the contact lens was driven by a driving board with antenna and RF transmission processing functions.

Figure 7:
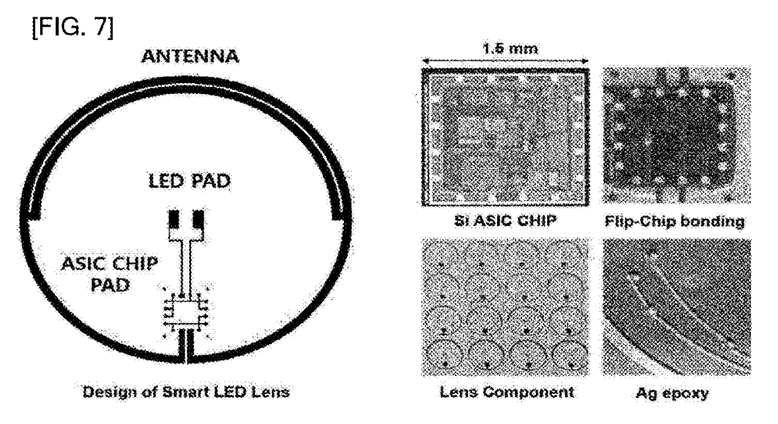
FIG. 7 shows examples of ASICs and electronic elements, configured on a plastic substrate.

FIG. 7 shows examples of ASICs and electronic elements, configured on a plastic substrate.

Specifically, FIG. 7 shows a design (left) and images after flip-chip bonding on a flexible transparent substrate and Ag epoxy bonding of an LED light source (right). Referring to FIG. 7, the result of flip-chip bonding of a pattern-bonded ASIC on the transparent substrate can be confirmed. In addition, electrical elements such as an LED light source, a capacitor, a battery and a resistor are bonded using Ag epoxy and then their operating states were confirmed.

Figure 8:
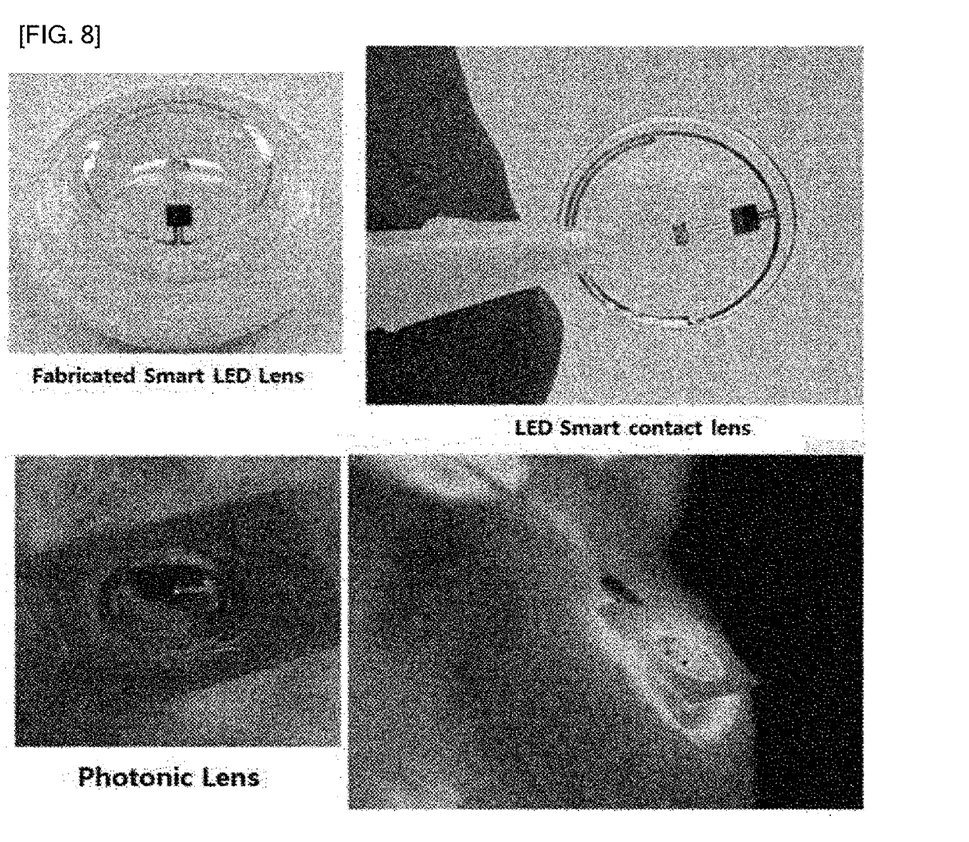
FIG. 8 shows a fabricated contact lens and its driving example.

In addition, FIG. 8 shows a fabricated contact lens and its driving example.

After applying the hyaluronic acid-Rose Bengal conjugate to a rabbit eye, it can be confirmed that the LED-equipped smart contact lens can be worn to be applied in injured corneal crosslinking, keratoconus treatment or vision correction. In addition, through thermal imaging camera analysis, it was confirmed that there is no problem in safety since a change in intraocular temperature is less than 1° C. even when the LED is driven.

INDUSTRIAL APPLICABILITY

The system according to the present invention may be used in crosslinking of injured corneas, and treatment of keratoconus or an injured cornea, and also be used for a wide range of vision correction.

The invention claimed is:

1. A system for injured cornea crosslinking, keratoconus treatment or vision correction, comprising:
    a hyaluronic acid-dye conjugate; and
    a contact lens including an LED light source.

2. The system of claim 1, wherein the hyaluronic acid is hyaluronic acid, a hyaluronic acid salt or a hyaluronic acid derivative, and
    a molecular weight of the hyaluronic acid is 10,000 to 3,000,000 daltons (Da).

3. The system of claim 1, wherein the dye is one or more selected from the group consisting of Rose Bengal, riboflavin, ethyl eosin, eosin Y, fluorescein, 2,2-dimethoxy, 2-phenylacetophenone, 2-methoxy, 2-phenylacetophenono, camphorquinone, methylene blue, erythrosine, Floxime, thionine and methylene green.

4. The system of claim 1, wherein the hyaluronic acid-dye conjugate is a conjugate in which a carboxyl group of hyaluronic acid and a carboxyl group of a dye are bonded through a linker.

5. The system of claim 4, wherein the linker is a diamine compound, which is one or more selected from the group consisting of diaminohexane (hexamethylenediamine), ethylenediamine, butylenediamine, pentaethylenehexaamine, and 1,5-diamino-2-methylpentane.

6. The system of claim 1, wherein the contact lens is based on one or more polymers selected from the group consisting of an elastomer such as a silicone elastomer; silicone hydrogel; polydiemthyloxane (MIMS); poly(2-hydroxyethylmethacrylate (PHEMA); and polyethylene glycol) methacrylate (PELMA).

7. The system of claim 1, wherein the contact lens has a flat surface.

8. The system of claim 1, wherein the LED light source emits light with a wavelength of 350 to 550 nm.

9. The system of claim 1, further comprising smart glasses, and
    wherein the contact lens is driven by an electrical signal transmitted from the smart glasses.

10. A method for injured cornea crosslinking, keratoconus treatment or vision correction by using the system for injured cornea crosslinking, keratoconus treatment or vision correction of claim 1, the method comprising:
    applying a hyaluronic acid-dye conjugate to a subject's cornea;
    wearing a contact lens including an LED light source; and
    irradiating the subject's cornea with light emitted from the LED light source in the contact lens.

* * * * *

UNITED STATES PATENT AND TRADEMARK OFFICE
CERTIFICATE OF CORRECTION

PATENT NO. : 12,403,326 B2
APPLICATION NO. : 17/642565
DATED : September 2, 2025
INVENTOR(S) : Hahn et al.

Page 1 of 1

It is certified that error appears in the above-identified patent and that said Letters Patent is hereby corrected as shown below:

In the Claims

Column 12, Line 37, Claim 6: Please correct "(MIMS)" to read --(PDMS)--

Column 12, Line 38, Claim 6: Please correct "polyethylene glycol" to read --poly(ethylene glycol)--

Column 12, Line 39, Claim 6: Please correct "(PELMA)" to read --(PEGMA)--

Signed and Sealed this
Ninth Day of December, 2025

John A. Squires
*Director of the United States Patent and Trademark Office*